United States Patent [19]

Thomas et al.

[11] Patent Number: 5,109,848
[45] Date of Patent: May 5, 1992

[54] ELECTROTHERAPEUTIC APPARATUS

[75] Inventors: Gary E. Thomas, Littleton; Michael W. Fellinger, Boulder, both of Colo.

[73] Assignee: PhysioDynamics, Inc., Littleton, Colo.

[21] Appl. No.: 355,167

[22] Filed: May 22, 1989

[51] Int. Cl.$^5$ .............................................. A61N 1/32
[52] U.S. Cl. .................................... 128/422; 128/421
[58] Field of Search .......... 128/421, 422, 423, 423 W, 128/419 C

[56] References Cited

U.S. PATENT DOCUMENTS

| | | | |
|---|---|---|---|
| 2,532,788 | 12/1950 | Sarnoff | 128/421 |
| 2,771,554 | 11/1956 | Gratzl | 128/421 |
| 3,640,284 | 2/1972 | De Langis | 128/422 |
| 3,833,005 | 9/1974 | Wingrove | 128/419 PG |
| 3,908,669 | 9/1975 | Man et al. | 128/422 |
| 4,019,519 | 4/1977 | Geerling | 128/422 |
| 4,071,033 | 1/1978 | Nawracaj et al. | 128/420 |
| 4,121,594 | 10/1978 | Miller et al. | 128/422 |
| 4,153,061 | 5/1979 | Nemec | 128/420 |
| 4,305,402 | 12/1981 | Katims | 128/732 |
| 4,374,524 | 2/1983 | Hedek, deceased et al. | 128/420 |
| 4,392,496 | 7/1983 | Stanton | 128/423 |
| 4,535,777 | 8/1985 | Castel | 128/421 |
| 4,580,570 | 4/1986 | Sarrell et al. | 128/421 |
| 4,690,145 | 9/1987 | King-Smith et al. | 128/421 |
| 4,719,922 | 1/1988 | Padjen et al. | 128/421 |
| 4,763,656 | 8/1988 | Nauman | 128/421 |
| 4,850,357 | 7/1989 | Bach, Jr. | 128/419 D |

FOREIGN PATENT DOCUMENTS

| | | | |
|---|---|---|---|
| 1169669 | 7/1985 | U.S.S.R. | 128/421 |
| 0773082 | 4/1957 | United Kingdom | 128/421 |

OTHER PUBLICATIONS

D. Gilbert, *The Miracle Machine*, pp. 175-183 (1980).
G. Taubes, "An Electrifying Possibility", *Discover*, Apr. 1986, at 22-26 and 30-37.
J. Guyon, "New Wrinkle in Search for Youth", *The Wall Street Journal*, Mar. 22, 1989, at B1.
"Electrostim 180-2i" Literature, Electrostim U.S.A. Ltd., date unknown.

Primary Examiner—William E. Kamm
Assistant Examiner—Kennedy J. Schaetzle
Attorney, Agent, or Firm—Sheridan Ross & McIntosh

[57] ABSTRACT

The present invention provides an electrotherapeutic apparatus that produces a signal that, upon application to a patient, is exponential in character. The signal includes a relatively low-frequency, constant amplitude, periodic-exponential signal for muscle stimulation. Further, the signal preferably includes a relatively high-frequency, periodic-exponential signal for sensory stimulation.

32 Claims, 2 Drawing Sheets

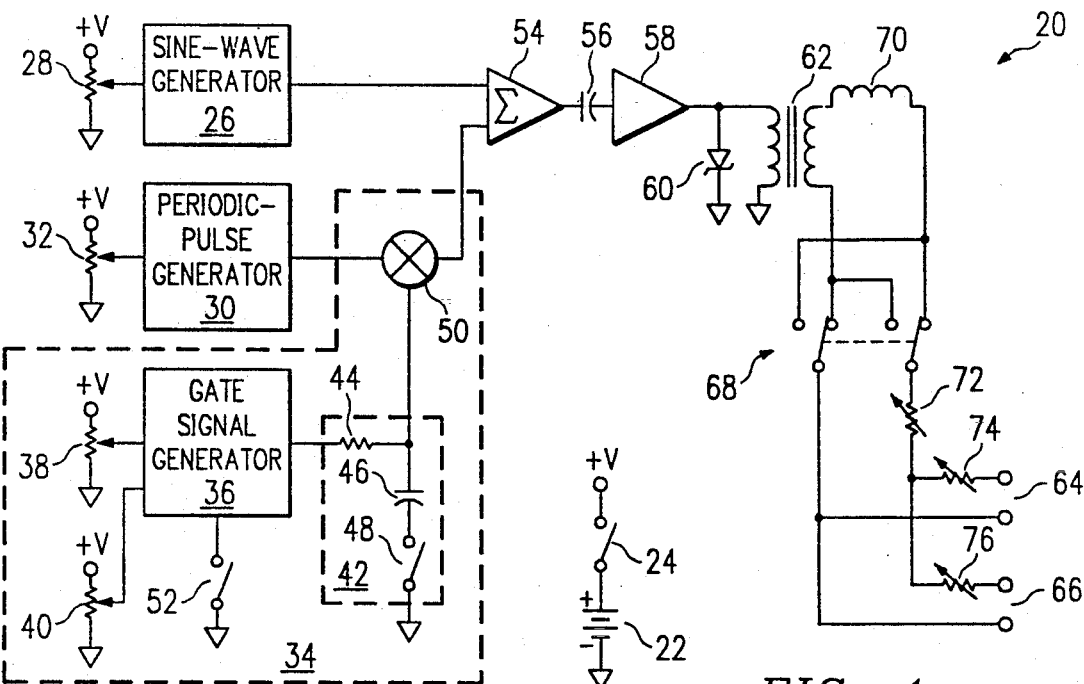
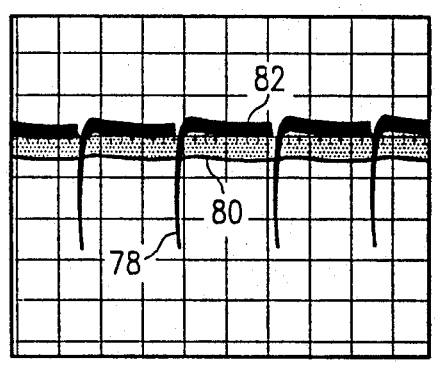
FIG. 2B
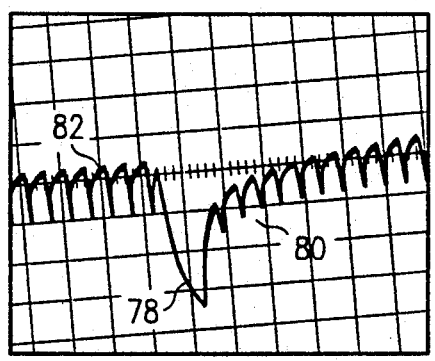
FIG. 2C
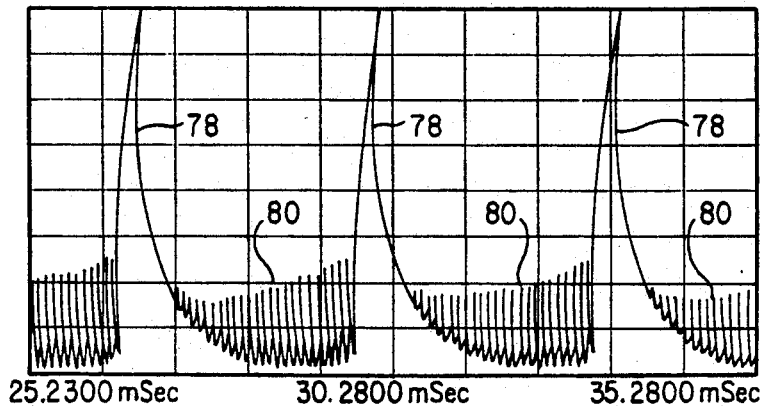
FIG. 2A

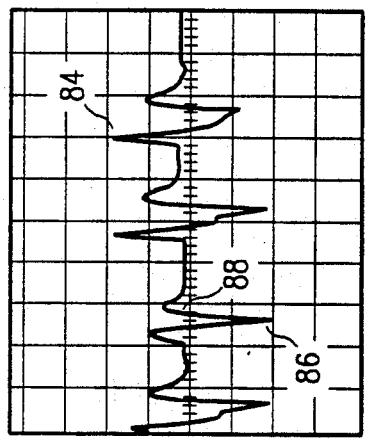
FIG. 3
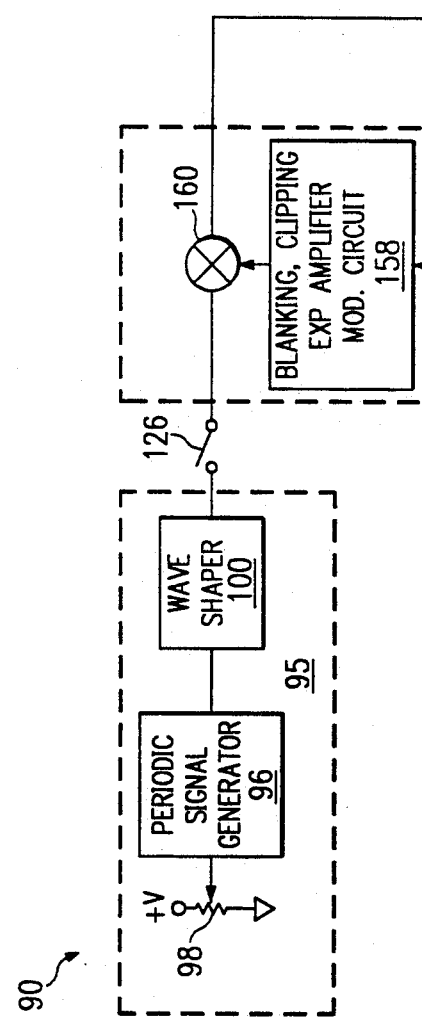
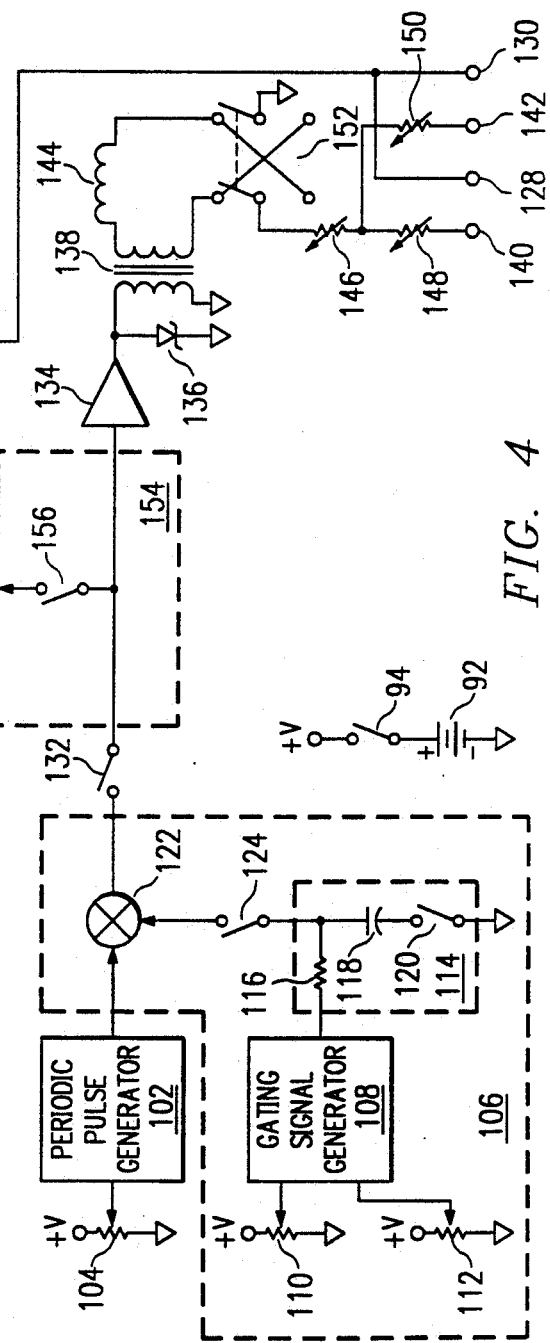
FIG. 4

ELECTROTHERAPEUTIC APPARATUS

FIELD OF THE INVENTION

The present invention relates to an apparatus and method for providing electrical stimulation to a patient.

BACKGROUND OF THE INVENTION

Among the known types of apparatuses for applying an electrical stimulation to a patient is the interference type apparatus that is used to stimulate structures located within the patient's body, such as muscles and/or the nerves that control muscle action, that are reached with relatively high frequency signals, but are responsive to relatively low frequency signals. The interference apparatus operates by applying two primary signals of relatively high, but slightly different, frequencies to the patient's body. The primary signals, due to their relatively high frequency, penetrate the patient's body and reach the aforementioned structures where they intersect and produce a beat signal having a relatively low frequency that is equal to the slight difference in the frequencies of the primary signals. Exemplary of known interference type apparatuses is U.S. Pat. No. 4,374,524 to Hudek (1983) which illustrates the use of a square-wave signal generator in conjunction with a plurality of phase-locked loops and low-pass filters to produce a plurality of sine-wave, primary signals. Also representative of known interference type apparatuses are U.S. Pat. No. 4,071,033 to Nawracaj et al. (1978), and U.S Pat. No. 4,153,061 to Nemec (1979) which, in addition to providing two primary signals of different frequencies, also amplitude modulate the primary signals to achieve various therapeutic effects. For example, in Nawracaj two square-wave, primary signals are amplitude modulated by either a square-wave, ramp, exponential, semi-sine or sine-wave signal. In Nemec two sine-wave, primary signals are modulated by two low-frequency sine-wave signals to achieve stimulation at the point of application to the patient's body in addition to producing a beat signal therein.

Another known type of apparatus for applying an electrical stimulation to a patient's body is exemplified in U.S. Pat. No. 4,392,496 to Stenton (1983). Stenton applies two, apparently, square-wave signals to a patient's body in an alternating fashion to achieve muscle stimulation and prevent disuse atrophy. Further, in order to achieve optimal muscle stimulation and enhance the comfort of the patient, Stenton provides for the adjustment of several parameters associated with the applied signals, such as amplitude and frequency.

Yet another apparatus for administering an electrical stimulation to a patient's body is illustrated in U.S. Pat. No. 4,580,570 to Sarrell et al. (1986). The method of Sarrell is characterized by the application of pulses that have a relatively high voltage, high peak but low average current, and short duration. Moreover, the apparatus of Sarrell can be adjusted to apply the aforementioned pulses continuously, periodically, or in an alternating fashion.

Typically, the patient's body produces electrical signals, in the form of sensory and muscle nerve impulses, that are exponential in character. Characteristic, however, of the foregoing apparatuses is the application of signals, like sine-waves and square-waves, that are alien to the typical patient's body. Consequently, the patient can experience a certain amount of discomfort. Moreover, exposure to such alien signals can traumatize certain biological structures associated with the patient. Consequently, there exists a need for an electrotherapeutic device that produces a signal or signals that more closely resemble the exponential character of the patient's natural signals. There also exists a need for an electrotherapeutic device that produces a signal capable of penetrating the patient's body and that reduces any trauma imposed upon biological structures associated with the patient's body.

SUMMARY OF THE INVENTION

The present invention provides an electrotherapeutic apparatus for applying an electrical stimulation to a patient's body. The apparatus includes a device for producing a periodic-exponential signal, that is more suitable for application to a patient's body, and a device for applying the signal to the patient's body.

One embodiment of the apparatus includes devices for generating a relatively high-frequency sine-wave signal, suitable for sensory stimulation, and a relatively low-frequency pulse signal suitable for muscle stimulation. Furthermore, this embodiment includes a device for summing the low-frequency sine-wave and high-frequency pulse signal into a sum signal. The apparatus further includes a device for exponentially shaping the sum signal. The apparatus also includes a device for applying the sum signal to the patient's body. Preferably, the apparatus includes a device that blanks or attenuates the high-frequency portion of the sum signal when a pulse associated with the low-frequency pulse signal is present in the sum signal. Furthermore, the apparatus preferably includes a device for exponentially amplitude modulating the high-frequency portion of the sum signal. Additionally, the apparatus preferably includes a device for clipping the high-frequency portion of the sum signal.

A second embodiment of the apparatus includes devices for generating a first periodic-exponential signal having a frequency suitable for sensory stimulation and a second periodic-exponential signal having a frequency suitable for motor stimulation. The apparatus further includes switches for allowing an operator to apply either the first signal, second signal or both signals to the patient's body. Moreover, the apparatus includes a device for, at the operator's discretion, blanking the first signal during the presence of a pulse associated with the second signal and clipping together with exponentially amplitude modulating the first signal otherwise.

The present invention also provides a method for providing electrical stimulation to a patient. The method includes the steps of generating a periodic exponential signal and applying it to the patient.

BRIEF DESCRIPTION OF THE DRAWINGS

FIG. 1 illustrates a first embodiment of the invention;

FIG. 2A illustrates several cycles of the sum signal that is applied to a patient's body by the first embodiment of the invention shown in FIG. 1;

FIG. 2B illustrates a portion of a single cycle of the sum signal that is applied to a patient's body by the first embodiment of the invention shown in FIG. 1;

FIG. 2C illustrates the substantially constant amplitude periodic-exponential portion of the sum signal that is applied to a patient's body by the first embodiment of the invention shown in FIG. 1;

FIG. 3 shows the signal naturally produced by a human patient;

FIG. 4 illustrates a second embodiment of the invention.

DETAILED DESCRIPTION

With reference to FIG. 1, a first embodiment of the invention, the electrotherapeutic apparatus 20 (hereinafter referred to as the apparatus 20), is illustrated. The apparatus 20 generates a periodic-exponential signal that is applied to a patient in order to stimulate one or more muscles. The apparatus also, preferably, generates a periodic-exponential signal that causes sensory stimulation. The term patient as used herein includes vertebrate animals, such as humans, horses, cattle, dogs, cats, birds, snakes and the like.

The apparatus 20 includes a power supply 22, preferably a six-volt battery, for providing operating voltages to the remainder of the apparatus 20. A power supply switch 24 allows an operator to selectively turn "on" and "off" the apparatus 20 by, respectively, connecting and disconnecting the power supply 22 from the remainder of the apparatus 20.

The apparatus 20 further includes a sine-wave generator 26 for producing a constant amplitude sine-wave signal with a frequency of approximately 10-kHz. The 10-kHz sine-wave signal is within the frequency range that is typically used to stimulate the sensory nerves of a patient, i.e., in the range of about 1,000–100,000 Hz. If frequencies outside of this range are found to provide sensory stimulation to the patient, then the frequency of the sine-wave signal produced by the sine-wave generator 26 can be adjusted accordingly. Adjustment of the amplitude of the sine-wave signal is, at least in part, achieved by a first rheostat 28. Preferably, the first rheostat 28 is adjusted when the apparatus 20 is manufactured and is thereafter inaccessible to an operator of the apparatus 20.

The apparatus 20 further includes a periodic-pulse generator 30 for producing a constant amplitude periodic-pulse signal with a frequency ranging from 40 Hz to 500 Hz. The frequency of the periodic-pulse signal encompasses the frequency spectrum that is generally used to stimulate the muscles of a patient, i.e. D.C. to 1,000 Hz. If frequencies outside of this range are found to provide muscle stimulation to the patient, then the frequency of the periodic-pulse signal produced by the periodic-pulse generator 30 can be adjusted accordingly. Adjustment of the frequency of the periodic-pulse signal is provided by a second rheostat 32.

Also included in the apparatus 20 is a gating means 34 for selectively gating the periodic-pulse signal produced by the periodic-pulse generator 30 in a periodic fashion. In other words, the gating means 34 operates to alternatingly allow and inhibit the passage of the stimulation periodic-pulse signal to the animal patient's body. The preferred gating means 34 includes a gating signal generator 36 for producing a periodic-pulse signal, hereinafter referred to as the gating signal. The period of the gating signal can be adjusted from approximately five seconds to one minute by a third rheostat 38. A fourth rheostat 40 allows the duty cycle of the gating signal to be adjusted from about five percent to about ninety-five percent. Further included in the preferred gating means 34 is a gradual on-off means 42 for selectively smoothing the rising and falling edges of the gating signal thereby producing the effect of gradually allowing and inhibiting the passage of the stimulation signal. The preferred gradual on/off means 42 includes a resistor 44 and a capacitor 46 which, when a first switch 48 is closed, act as a low-pass filter that smooths the rising and falling edges of the gating signal. The preferred gating means 34 further includes a multiplier 50 for alternatingly allowing and inhibiting the passage of the periodic-pulse signal output by the periodic-pulse generator 30 according to the gating signal. For example, if the gating signal is zero then the multiplier 50 inhibits the passage of the periodic-pulse signal. If, on the other hand, the gating signal is non-zero, then the multiplier 50 allows the periodic-pulse signal or a portion thereof to pass. Additionally, the preferred gating means 34 includes a second switch 52 for allowing an operator to selectively allow or inhibit the gating signal from reaching the multiplier 50. In other words, the second switch 52 gives the operator the option of using or not using the gating apparatus 34. Specifically, when the second switch 52 is open, the gating signal is applied to the multiplier 50 and the periodic-pulse signal is gated accordingly. When the second switch 52 is closed, the gating signal is not applied to the multiplier 50 and the multiplier 50 allows the periodic-pulse signal to pass unattenuated.

The apparatus 20 further includes a summing amplifier 54 for adding the sine-wave signal produced by the sine-wave generator 26 and the periodic-pulse signal output by the multiplier 50 to produce a sum signal. One cycle of the sum signal, less any DC component, includes a first portion and a second portion. The first portion reflects the sum of the sine-wave signal and the pulse portion of the periodic-pulse signal. The second portion reflects the sum of the sine-wave signal and the portion of the periodic-pulse signal when the pulse is absent. Since the periodic-pulse signal is zero when the pulse is absent, the second portion of the sum signal is, essentially, just the sine-wave signal.

Apparatus 20 further includes an AC coupling capacitor 56 and, a power amplifier 58 and a zener diode 60. The AC coupling capacitor 56 serves, at least in part, to eliminate any DC component in the sum signal output by the summing amplifier 54. The AC coupling capacitor 56 can be either a discrete component or the capacitance associated with the power amplifier 58 can be used. Similarly, the zener diode 60 can be either a discrete component or the breakdown characteristics of the power amplifier 58 can be employed. Preferably, the AC coupling capacitor 56 and the zener diode 60 are realized by using the capacitance and breakdown characteristics of the power amplifier 58, respectively. Consequently, the AC coupling capacitor 56 and zener diode 60 shown in FIG. 1 are representative of the capacitance and breakdown characteristics of the power amplifier 58. The operation of the capacitor 56, power amplifier 58 and zener diode 60 is now described during the first and second portions of a single cycle of the sum signal output by the summing amplifier 54. The first portion of the sum signal passes through the capacitor 56 to the power amplifier 58 where it drives the power amplifier 58 into the cutoff region. When the power amplifier 58 is in the cutoff region it does not output any current. The zener diode 60, however, cooperates with a transformer to maintain a defined voltage at the output of the power amplifier 58 for the duration of the first portion of the sum signal. Further, the zener diode 60 operates to blank out a substantial portion of the sine-wave signal aspect of the first portion of the sum signal. Consequently, a pulse having the defined voltage is produced at the output of the power amplifier 58 even though the power amplifier is operating in the cutoff region. In addition, while the power amplifier 58 is in cutoff, the bias voltage supplied by the power supply 22 charges the capacitor 56. The second portion of the sum signal is substantially unaffected by the operation of the zener diode 60. The capacitor 56 and the power amplifier 58 do, however, affect the second portion of the sum signal. Specifically, the capacitor 56 passes the second portion of the sum signal on to the power amplifier 58 and discharges the charge accumulated during the first portion of the sum signal into the power amplifier 58 in an exponential fashion. The discharging of the capacitor 56 results in the second portion of the sum signal being exponentially amplitude modulated. Once the capacitor 56 is completely discharged, exponential amplitude modulation of the second portion of the sum signal ceases and a constant amplitude steady state is attained. The second portion of the sum signal also drives the power amplifier into saturation during a portion of each cycle of the sine-wave signal that comprises the second portion of the sum signal. Consequently, the power amplifier 58 also clips a portion of each cycle of the sine-wave signal. In summary, the one cycle of the sum signal produced at the output of the power amplifier 58 includes a pulse, the first portion, and a clipped sine-wave signal that is, for a time, exponentially amplitude modulated the second portion.

The apparatus 20 also preferably includes a step-up transformer for increasing the voltage of the sum signal existing at the output of the power amplifier 58. In the preferred embodiment the step-up transformer is a 1:10 step-up transformer 62. The sum signal at the output of the step-up transformer 62 is, following further processing discussed hereinafter, distributed to means for applying it to the patient. In the embodiment illustrated in FIG. 1, the sum signal output by the step-up transformer 62 is, in the preferred embodiment, distributed to a first pair of pads 64 and a second pair of pads 66 that are applied to the patient's skin. Alternatively, the sum signal can be distributed to applicators, such as point applicators, that can be moved over the patient's skin during treatment. Other means for applying the sum signal to the patient include an internal applicator that is inserted into the body of the patient, such as a needle electrode, and a remote applicator, such as a transmission antenna.

A double-pole, double-throw switch 68 allows an operator to change the polarity of the sum signal applied to the first and second pairs of pads 64, 66.

The apparatus 20 further includes a shaping means that is used to exponentially shape the sum signal output the transformer 62 and applied to the patient by the first pair of pads 64 and/or the second pair of pads 66. With reference to a single cycle of the sum signal, exponential shaping results in the rising and/or falling aspects of the first portion of the sum signal including an exponential component. Exponential shaping also, preferably, results in the rising and/or falling aspects of each cycle of the sine-wave signal comprising the second portion of the sum signal including an exponential component. Preferably, the shaping means is used to impart a double-exponential character to the sum signal where both the rising and falling edges of the first portion of the sum signal and each cycle of the sine-wave signal in the second portion of the sum signal include an exponential component. Preferably, the shaping means includes an inductor-resistor network comprising an inductor 70, a fifth rheostat 72, a sixth rheostat 74 and a seventh rheostat 76. The inductor 70 can be either a discrete component or incorporated into the transformer 62. The inductor 70, the fifth rheostat 72, sixth rheostat 74, seventh rheostat 76 and the electrical load provided by the patient cooperate to exponentially shape the sum signal existing at the first pair of pads 64. While not wishing to be bound by theory, it is believed that the following explanation correctly models the interaction of the shaping means and the patient in exponentially shaping the sum signal produced at the first pair of pads 64. The inductor 70, fifth rheostat 72 and sixth rheostat 74 define, at least in part, the "L/R" exponential time constant that determines the exponential character of the sum signal applied to the patient by the first pair of pads 64. The electrical load provided by the patient also defines, at least in part, the "L/R" exponential time constant that determines the exponential character of the sum signal applied to the patient by the first pair of pads 64. Specifically, the inductor 70 defines the "L" portion of the exponential time constant and the fifth rheostat, sixth rheostat and resistance provided by the patient across the first pair of pads 64 determines the "R" portion of the exponential time constant. The resistance across the first pair of pads 64 is substantially infinite when they are not attached to a patient. Consequently, the exponential time constant approaches zero and the sum signal output by the transformer 62 is substantially unaffected. If, however, the first pair of pads 64 are attached to a patient, then a non-zero exponential time constant is established and the sum signal is shaped accordingly. Specifically, the patient establishes a finite resistance across the first pair of pads 64 which, in combination with inductor 70, fifth rheostat 72 and sixth rheostat 74, defines a non-zero exponential time constant. Consequently, the exponential character of the sum signal applied to the patient is defined in part by the resistance provided by the patient, i.e., the sum signal accommodates to the patient. The patient is roughly modeled as a resistance in series with a large capacitor. The "RC" exponential time constant associated with the patient is relatively large with respect to the aforementioned "L/R" time constant. Consequently, the capacitance associated with the patient is relatively insignificant and can be ignored for purposes of explaining the interaction between the patient and the shaping means. Adjustment of the fifth rheostat 72 and/or the sixth rheostat 74 alters the exponential time constant and, hence, the exponential character of the sum signal applied to the patient by the first pair of pads 64. In addition, adjustment of the fifth rheostat 72 and/or the sixth rheostat 74 affects the amplitude of the sum signal applied to the patient by the first pair of pads 64. The inductor 70, fifth rheostat 72 and seventh rheostat 76 operate in an identical fashion with respect to the sum signal applied to the patient by the second pair of pads 66. A shaping means that does not interact with the electrical load provided by the patient is also feasible.

FIGS. 2A and 2B illustrate the sum signal applied to a patient by either the first pair of pads 64 or the second pair of pads 66 with the double-pole, double-throw switch 68 in a first orientation. The sum signal includes a substantially constant amplitude, periodic-exponential portion 78 suitable for muscle stimulation. The sum signal also includes an exponentially amplitude modulated, clipped, periodic-exponential portion 80. As shown in FIGS. 2A-2C, the exponential amplitude modulation eventually terminates and a clipped, periodic-exponential signal 82 results. The clipped, periodic-exponential signal 82 show in FIG. 2C was produced with the double-pole, double-throw switch 68 in a second orientation. Consequently, the clipped, periodic-exponential signal 82 in FIG. 2C is the mirror image or opposite polarity of the corresponding clipped, periodic-exponential signals shown in FIGS. 2A and 2B.

FIG. 3 shows a natural signal 84 produced by a human patient. The natural signal 84 includes a double-exponential portion 86 that corresponds to the constant amplitude, periodic-exponential signal 78 produced by the apparatus 20. The natural signal 84 also includes an exponentially amplitude modulated portion 88 that corresponds to the exponentially amplitude modulated, clipped, periodic-exponential signal produced by the apparatus 20. Consequently, the sum signal produced by the apparatus 20 corresponds, at least in part, to the signal 84 naturally produced by the human patient.

Operation of the apparatus 20 includes an initialization phase where the power supply switch 24 is placed in the "off" position to insure that when the pads are subsequently applied to the patient an undesirable signal is not also applied to the patient. Initialization also involves setting the fifth, sixth and seventh rheostats 72, 74, 76 for maximum attenuation to insure that the minimum amplitude sum signal is applied to the patient when the power supply switch 24 is closed. Further, the second rheostat 32 is set such that the periodic-pulse generator 30 will produce a periodic-pulse signal having a frequency at or about the mid-range of possible frequencies when the power supply switch 24 is closed. Also during initialization, the third and fourth rheostats 38, 40, are set such that when the power supply switch 24 is closed, a gating signal will be produced by the gate signal generator 36 that has a frequency in the midrange of possible frequencies and a duty cycle of about fifty percent. During initialization, the second switch 52 is opened to insure that the gating signal is applied to the multiplier 50 when the power supply switch 24 is closed. Additionally, the first switch 48 is closed during initialization so that when the power supply switch 24 is closed the gating signal produced by the gate signal generator 36 is smoothed before application to the multiplier 50. Following initialization of the aforementioned switches and rheostats, the first pair of pads 64 and/or the second pair of pads 66 are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be placed on the dorsal part of the body. If it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 24 is closed and the apparatus 20 generates the sum signal comprising the substantially constant amplitude, periodic-exponential signal 78 and the exponentially amplitude modulated, clipped, periodic-exponential signal 80. The sum signal is applied to the patient via the pads. Due to the aforementioned adjustment of the fifth, sixth and seventh rheostats 72, 74, 76 the sum signal applied to the patient is of minimum amplitude. At this point the exponential character and amplitude of the sum signal being applied to the patient can be adjusted using the fifth rheostat 72 and the sixth or seventh rheostats 74, 76. In addition, the frequency of the periodic-pulse portion of the sum signal can be adjusted using the second rheostat 32. Adjustment of the frequency and duty cycle of the gating signal can be accomplished by manipulating the third and fourth rheostats 38, 40. If the gating signal is not desired, then the second switch 52 can be closed.

FIG. 4 illustrates a second embodiment of the invention, i.e., the electrotherapeutic apparatus 90 (hereinafter referred to as the apparatus 90). Apparatus 90, in contrast to apparatus 20, does not sum a sine-wave signal and a periodic-pulse signal. Rather, apparatus 90 applies the a periodic-exponential signal suitable for sensory stimulation and a periodic-exponential pulse signal suitable for muscle stimulation to the body of the patient over separate paths. The apparatus 90 allows an operator to control whether the periodic-exponential signal suitable for sensory stimulation, periodic-exponential pulse signal suitable for muscle stimulation or both signals are applied to the patient. The apparatus 90 also allows the operator to selectively blank, exponentially amplitude modulate, and clip the periodic-exponential signal used for sensory stimulation.

The apparatus 90 includes a power supply 92 and power supply switch 94 which operate in a substantially similar fashion to the power supply 22 and the power supply switch 24 of apparatus 20.

The apparatus 90 further includes a periodic-exponential signal generator 95 for producing a constant amplitude periodic-exponential signal having a frequency appropriate for stimulation of the sensory nerves of a patient. The preferred periodic-exponential signal generator 95 includes a periodic signal generator 96 for outputting a constant amplitude periodic signal. Preferably, the power associated with the periodic signal output by the periodic signal generator 96 is sufficient to penetrate the patient's body. Amplitude adjustment of the periodic signal output by the periodic signal generator 96 is provided by a first rheostat 98. Preferably, the first rheostat 98 is adjusted when the apparatus 90 is manufactured and is thereafter inaccessible. The periodic signal output by the periodic signal generator 96 can have virtually any shape since the preferred periodic-exponential generator 95 includes a wave-shaper 100 that is designed to modify the shape of whatever signal is being output by the periodic signal generator 96 to produce a constant amplitude periodic-exponential signal. For example, if the periodic signal generator 96 is outputting a constant amplitude square-wave signal, then the wave-shaper is designed to modify the square-wave shape to a periodic-exponential shape. Exponential shaping of the periodic signal output by the periodic signal generator results in the rising and/or falling aspects of the periodic signal having an exponential component. Preferably, the wave-shaper 100 imparts a double-exponential character to the periodic signal where both the rising and falling aspects have an exponential component.

The apparatus 90 further includes a periodic-pulse signal generator 102 for generating a periodic-pulse signal having a frequency suitable for muscle or motor stimulation of a patient. The frequency of the stimulation pulse signal output by the stimulation periodic-pulse signal generator 102 is adjusted by manipulating a second rheostat 104.

The apparatus 90 further includes a gating means 106 that alternatingly allows and inhibits the passage of the periodic-pulse signal. The preferred gating means 106 includes a gating signal generator 108 for producing a gating signal. The period and duty cycle of the gating signal produced by the gating signal generator 108 can be adjusted by, respectively, a third rheostat 110 and a fourth rheostat 112. A gradual on/off means 114, preferably comprising a resistor 116, a capacitor 118 and a first switch 120, provides an operator with the option of smoothing the rising and falling edges of the gate signal such that the periodic-pulse signal is gradually applied and then removed from the patient. A first multiplier 122 gates the periodic-pulse signal produced by the periodic-pulse signal generator 102 according to the gating signal. A second switch 124 provides an operator with the option of using or not using the gating apparatus 106.

The apparatus 90 further includes a third switch 126 that gives an operator with the option of providing or not providing the background periodic-exponential signal output by the wave-shaper 100 to a means for applying the signal to the patient. Specifically, if the third switch 126 is open then the periodic-exponential signal is not applied to the patient. When the third switch 126 is closed, the periodic-exponential signal is applied to the patient using one or more pads attached to the patient's skin. Preferably, a first pad 128 and a second pad 130 are employed to apply the periodic-exponential signal to the patient. Alternatively, the periodic-exponential can be applied to the patient's skin using a point applicator that can be moved over the patient's skin during treatment. Other means for applying the periodic-exponential signal to the patient include an internal applicator, such as a needle electrode inserted into the body of the patient, and a remote applicator, like a transmission antenna.

The apparatus 90 further includes a fourth switch 132 for providing an operator with the option of applying or not applying the periodic-pulse signal to the patient. Specifically, when the fourth switch 132 is open, the stimulation periodic-pulse signal is not applied to the patient. However, when the fourth switch 132 is closed, the periodic-pulse signal output by the first multiplier 122 is applied to a power amplifier 134 which amplifies the periodic-pulse signal. The amplified periodic-pulse signal is then applied to a regulator, which in the preferred embodiment is a zener diode 136. The zener diode 136 can be a discrete component or the breakdown characteristic of the power amplifier 134 can be employed. Once processed by the zener diode 136, the periodic-pulse signal is applied to a step-up transformer for increasing the voltage of the periodic-pulse signal. In the preferred embodiment of apparatus 90, a 1:10 step-up transformer 138 is used.

The periodic-pulse signal output by the transformer 138 is, following processing described more thoroughly hereinafter, distributed to means for applying it to the patient. In the embodiment illustrated in FIG. 4, the periodic-pulse signal is applied to a patient using one or more pads attached to the patient's skin. Preferably, a third pad 140 and a fourth pad 142 are used to apply the periodic-pulse signal to the patient. Alternatively, the periodic-pulse signal can be applied to the patient's skin using a point applicator that can be moved over the patient's skin during treatment. Other means for applying the periodic-pulse signal to the patient include a device inserted into the interior of the patient's body, like a needle electrode, and a remote applicator, like a transmission antenna.

The apparatus 90 further includes a shaping means that is used to exponentially shape the periodic-pulse signal output by the transformer 138 and applied to the patient by the third and fourth pads 140, 142. Exponential shaping of the periodic-pulse signal results in the rising and/or falling aspects of the pulse in the periodic-pulse signal include an exponential component. Preferably, the shaping means imparts a double-exponential character to the periodic-pulse signal where both the rising and falling of the pulse in each cycle of the periodic-pulse signal include an exponential component. Preferably, the shaping means includes an inductor-resistor network comprising an inductor 144, a fifth rheostat 146, a sixth rheostat 148, and a seventh rheostat 150. The inductor 144 can be either a discrete component or incorporated into the transformer 138. The inductor-resistor network operates, as previously discussed with respect to apparatus 20, to modify the periodic-pulse signal output by the transformer 138 such that the periodic-pulse signals applied to the patient by the third and fourth pads 140, 142, are constant amplitude periodic-exponential signals.

A double-pole, double throw switch 152 allows an operator to change the polarity of the constant amplitude periodic-exponential signals applied to the patient by the third and fourth pads 140, 142.

The apparatus 90 also includes a blanking, clipping and exponentially amplitude modulating circuit 154 for blanking the periodic-exponential signal output by the wave shaper 100 when a pulse associated with the periodic-exponential signal output by the multiplier 122 is present and clipping, together with exponentially amplitude modulating, the periodic-exponential signal otherwise. The blanking, clipping and exponentially amplitude modulating circuit 154 is comprised of a fifth switch 156, a blanking, clipping and exponential amplitude modulating signal generator 158 and a second multiplier 160. The blanking, clipping and exponential amplitude modulating circuit 154 operates such that when the fifth switch 156 is closed, the blanking, clipping and exponentially amplitude modulating signal generator 158 produces a signal that, upon application to the second multiplier 160, results in the periodic-exponential signal being blanked during the presence of a pulse associated with the periodic-exponential pulse signal. When the periodic-exponential signal is not blanked due to the presence of a pulse associated with periodic-exponential pulse signal it is clipped and exponentially amplitude modulated.

With reference to FIGS. 2A–2C, the various signals that can be applied to the patient by manipulation of the third switch 126 and the fourth switch 132 are illustrated. When the third switch 126 is closed and the fourth switch 132 is open, a constant amplitude, periodic-exponential signal 82 having a frequency suitable for sensory stimulation is applied to the patient. When the third switch 126 is open and the fourth switch 132 is closed, a constant amplitude periodic-exponential signal 78 having a frequency suitable for muscle stimulation is applied to the patient. When both the third switch 126 and the fourth switch 132 are closed, both of the constant amplitude, periodic-exponential signal 78 and the periodic-exponential signal 82 are applied to the patient. Further, if both the third switch 126 and the fourth switch 132 are closed, then the fifth switch can be closed to blank, clip and exponentially amplitude modulate the periodic-exponential signal 82. Once the appropriate signal or signals have been selected then the operator can manipulate the rheostats to further modify the signal or signals being applied to the patient.

Operation of the apparatus 90 includes an initialization phase where the power supply switch 94 is placed in the "off" position to insure that when the pads are subsequently applied to the patient an undesirable signal is not also applied to the patient. Initialization also involved setting the fifth, sixth and seventh rheostats 146, 148, 150 for maximum attenuation to insure that the minimum amplitude periodic-exponential signal, if selected, is applied to the patient upon the closing of the power supply switch 94. Further, the second rheostat 104 is set such that the periodic-pulse generator 102 produces a periodic-pulse signal having a frequency at or about the mid-range of possible frequencies. Also during initialization the third and fourth rheostats 110, 112, are set such that upon the closing of the power supply switch 94 a gating signal is produced by the gate signal generator 108 that has a frequency in the mid-range of possible frequencies and a duty cycle of fifty percent. During initialization, the second switch 124 is closed to insure that the gating signal is applied to the multiplier 122 when the power supply switch 94 is closed. Additionally, the first switch 120 is closed during initialization so that when the power supply switch 94 is closed the gating signal produced by the gate signal generator 108 is smoothed before application to the multiplier 50. Also during initialization of the third switch 126, fourth switch 132 and fifth switch 156 are opened or closed depending upon what type of signal is desired. Following initialization of the aforementioned switches and rheostats, one or more of the pads are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be placed on the dorsal part of the body. If it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 94 is closed and the desired signal is generated by the apparatus 90 and applied to the patient via the pads. Due to the aforementioned adjustment of the fifth, sixth and seventh rheostats 146, 148, 150 the periodic-pulse signal, if applied to the patient, is of a minimum amplitude. If the periodic-exponential pulse signal is applied to the patient, its amplitude can be adjusted using the fifth, sixth and seventh rheostats 146, 148, 150. In addition, the frequency of the periodic-exponential pulse can be adjusted using the second rheostat 104. Further, if the gating signal is being used, its frequency and duty cycle can be adjusted by manipulating the third and fourth rheostats 110, 112. If the gating signal is not desired, then the second switch 124 can be opened.

The electrotherapeutic apparatuses of the present invention can be useful in: (a) the relaxation of muscle spasms; (b) the prevention or retardation of muscle disuse atrophy; (c) increasing local blood circulation; (d) the re-education of muscles; (e) immediate post surgical stimulation of calf muscles to prevent venous thrombosis; and (f) maintaining or increasing the range of motion of limbs. As indicated hereinabove, the instant invention is particularly useful for muscle stimulation.

Generally in conducting a treatment using the present invention, it is preferred to apply the signal at a power setting which is past the point of complete comfort to the patient but is below the threshold of pain.

The foregoing description of the invention has been presented for purposes of illustration and description. Further, the description is not intended to limit the invention to the form disclosed therein. Consequently, variations and modifications commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternative embodiments to the extent permitted by the prior art.

What is claimed is:

1. An apparatus for providing electrical stimulation to a patient, comprising:
   means for use in providing a signal
   including a first portion having a first frequency and a second portion having a second frequency that is different than said first frequency,
   said second portion is substantially blanked when at least a portion of a pulse associated with said first portion is present, and
   at least one of said first portion and said second portion of said signal has a double-exponential shape; and
   means for applying said signal to the patient.

2. An apparatus for providing electrical stimulation to a patient, comprising:
   means for use in providing a signal
   including a first portion having a first frequency and a second portion having a second frequency that is different than said first frequency,
   said second portion is substantially blanked when at least a portion of a pulse associated with said first portion is present, and
   said second portion of said signal has an exponentially modulated amplitude; and
   means for applying said signal to the patient.

3. An apparatus for providing electrical stimulation to a patient, comprising:
   means for use in providing a signal
   including a first portion having a first frequency and a second portion having a second frequency that is different than said first frequency;
   said second portion is substantially blanked when at least a portion of a pulse associated with said first portion is present, and said second portion of said signal is clipped; and means for applying said signal to the patient.

4. An apparatus for providing electrical stimulation to a patient, comprising:
   means for use in providing a periodic-exponential signal;

wherein said means for use in providing a periodic-exponential signal includes means for use in providing a first periodic-exponential signal and means for use in providing a second periodic-exponential signal having a frequency between about 1000 Hz and 100,000 Hz; and means for applying said periodic-exponential signal to the patient.

5. An apparatus, as claimed in claim 4, further including:

means for exponentially amplitude modulating said second periodic-exponential signal.

6. An apparatus, as claimed in claim 4, wherein:
said second periodic-exponential signal is a second periodic, double-exponential signal.

7. An apparatus, as claimed in claim 4, wherein:
said second periodic-exponential signal is a second substantially constant peak amplitude periodic-exponential signal.

8. An apparatus, as claimed in claim 4, wherein:
said second periodic-exponential signal is a second periodic-exponential, clipped signal.

9. An apparatus for providing electrical stimulation to a patient, comprising:

means for use in providing a periodic-exponential signal;

wherein said means for use in providing a periodic-exponential signal includes means for use in providing a first periodic-exponential signal and means for use in providing a second periodic double-exponential signal having a frequency suitable for sensory stimulation; and means for applying said periodic-exponential signal to the patient.

10. An apparatus for providing electrical stimulation to a patient, comprising:

means for use in providing a periodic-exponential signal;

wherein said means for use in providing a periodic-exponential signal includes means for use in providing a first periodic-exponential signal and means for use in providing a second periodic-exponential clipped signal having a frequency suitable for sensory stimulation; and means for applying said periodic-exponential signal to the patient.

11. An apparatus for providing electrical stimulation to a patient, comprising:

means for use in providing a signal including a first portion having a first frequency and a second portion having a second frequency that is different than said first frequency, and said second portion is substantially blanked when at least a portion of a pulse associated with said first portion is present, said means for use in providing a signal includes exponential time constant means, and means for applying said signal to the patient.

12. An apparatus, as claimed in claim 11, wherein:
said exponential time constant means includes an inductor-resistor means.

13. An apparatus for providing electrical stimulation to a patient, comprising:

means for use in providing a periodic-exponential signal;

wherein said means for use in providing a periodic-exponential signal includes exponential time constant means;

wherein said exponential time constant means includes an inductor-resistor means;

wherein said inductor-resistor means includes variable resistor means for adjusting the exponential time constant of said periodic-exponential signal; and means for applying said periodic-exponential signal to the patient.

14. An apparatus for providing an electrical stimulation to a patient, comprising:

means for use in providing a first periodic-exponential signal having a frequency suitable for muscle stimulation;

means for applying said first periodic-exponential signal to the patient;

means for use in providing a second periodic-exponential signal having a frequency suitable for sensory stimulation and different from said frequency suitable for muscle stimulation; and means for use in applying said second periodic-exponential signal to the patient.

15. An apparatus for providing an electrical stimulation to a patient, comprising:

means for use in providing a first periodic-exponential signal having a first frequency;

means for use in providing a second periodic-exponential signal having a second frequency that is different than said first frequency;

means for summing said first and second periodic-exponential signals to produce a sum signal said means for summing including means for substantially blanking so that, when at least a portion of a pulse associated with said second periodic-exponential signal is present, said first periodic-exponential signal is substantially blanked; and means for applying said sum signal to the patient.

16. An apparatus, as claimed in claim 15, wherein:
said first frequency is a frequency suitable for muscle stimulation.

17. An apparatus, as claimed in claim 15, wherein:
said first periodic-exponential signal has a substantially constant peak amplitude.

18. An apparatus, as claimed in claim 15, wherein:
said second frequency is a frequency suitable for sensory stimulation.

19. An apparatus, as claimed in claim 15, wherein:
said second periodic-exponential signal has a substantially constant peak amplitude.

20. An apparatus, as claimed in claim 15, wherein:
said second periodic-exponential signal is exponentially amplitude modulated.

21. An apparatus for providing an electrical stimulation to a patient, comprising:

means for use in providing a first periodic-exponential signal;

means for use in providing a second periodic double-exponential signal that has a frequency suitable for sensory stimulation;

means for summing said first and second periodic-exponential signals to produce a sum signal; and means for applying said sum signal to the patient.

22. An apparatus for providing an electrical stimulation to a patient, comprising:

means for use in providing a first periodic-exponential signal;

means for use in providing a second periodic-exponential signal;

means for summing said first and second periodic-exponential signals to produce a sum signal said means for summing including means for substantially blanking so that said second periodic-exponential signal is blanked when a pulse associated with said first periodic-exponential signal is present in said sum signal; and means for applying said sum signal to the patient.

23. An apparatus for providing an electrical stimulation to a patient, comprising:
means for use in providing a first periodic double-exponential signal;
that has a frequency suitable for muscle stimulation;
means for use in providing a second periodic-exponential signal;
means for summing said first and second periodic-exponential signals to produce a sum signal; and
means for applying said sum signal to the patient.

24. An apparatus for providing an electrical stimulation to a patient, comprising:
means for use in providing a first periodic-exponential signal;
means for use in providing a second periodic-exponential clipped signal;
means for summing said first and second periodic-exponential signals to produce a sum signal; and
means for applying said sum signal to the patient.

25. An apparatus for providing an electrical stimulation to a patient, comprising:
means for use in providing a first periodic signal;
means for use in providing a second periodic signal;
means for summing said first and second periodic signals to produce a sum signal having a first periodic signal portion and a second periodic signal portion, wherein said sum signal is other than a periodic exponential sum signal;
means for use in altering said sum signal to produce a periodic-exponential sum signal; and
means for applying said periodic-exponential sum signal to the patient.

26. An apparatus, for providing an electrical stimulation to a patient, comprising:
means for use in providing a periodic-exponential signal having a first portion with a first frequency and a second portion with a second frequency that is different than said first frequency, and
said first portion is substantially blanked when at least a portion of a pulse associated with said second portion is present; and
means for applying said periodic-exponential to the patient wherein the electrical load provided by the patient defines, at least in part, the exponential character produced by said means for providing.

27. An apparatus for providing an electrical stimulation to a patient, comprising:
means for providing a substantially constant amplitude sine-wave signal having a frequency substantially between 1000 Hz and 100,000 Hz;
means for adjusting the amplitude of said sine-wave signal;
means for providing a first substantially constant amplitude pulse signal having a frequency substantially between 40 Hz and 500 Hz;
means for adjusting the frequency of said first substantially constant amplitude pulse signal;
means for selectively gating said first pulse signal, comprising:
means for providing a second pulse signal having a period;
means for adjusting the period of said second pulse signal;
means for adjusting the duty cycle of said second pulse signal; and
means for multiplying said first substantially constant amplitude pulse signal by said second pulse signal to periodically gate said first substantially constant amplitude pulse signal;
means for summing said substantially constant amplitude sine-wave signal and said first substantially constant amplitude pulse signal to produce a sum signal;
means for exponentially amplitude modulating said sum signal;
means for clipping said substantially constant amplitude sine-wave signal in said sum signal;
means for blanking said substantially constant amplitude sine-wave signal in said sum signal when a pulse of said first substantially constant amplitude pulse signal is in said sum signal;
means for adjustably modifying said sum signal to produce a periodic-exponential, sum signal;
means for changing the polarity of said periodic-exponential, sum signal; and
means for applying said periodic-exponential, sum signal to the patient at two locations.

28. A method for providing electrical stimulation to a patient, comprising:
generating a signal
including a first portion having a first frequency and a second portion having a second frequency that is different than said first frequency,
said second portion is substantially blanked when at least a portion of a pulse associated with said first portion is present, and
at least one of said first portion and said second portion of said signal has a double exponential shape; and
applying said periodic-exponential signal to the patient.

29. A method for providing electrical stimulation to a patient, comprising:
generating a periodic-exponential signal;
wherein said step of generating a periodic-exponential signal includes generating a first periodic-exponential signal and generating a second periodic double-exponential signal having a frequency suitable for sensory stimulation; and
applying said periodic-exponential signal to the patient.

30. A method for providing electrical stimulation to a patient, comprising:
generating a signal
including a first portion having a first frequency and a second portion having a second frequency that is different than said first frequency,
said second portion is substantially blanked when at least a portion of a pulse associated with said first portion is present, and
said second portion of said signal has an exponentially modulated amplitude; and
applying said periodic-exponential signal to the patient.

31. A method for providing electrical stimulation to a patient, comprising:
generating a periodic exponential signal including a first portion having a first frequency and a second portion having a second frequency that is different than said first frequency, said second portion is substantially blanked when at least a portion of a pulse associated with said first portion is present, and said second portion of said signal is clipped; and applying said periodic-exponential signal to the patient.

32. A method for providing electrical stimulation to a patient, comprising:

generating a periodic-exponential signal;

wherein said step of generating a periodic-exponential signal includes generating a first periodic-exponential signal and generating a second periodic-exponential clipped signal having a frequency suitable for sensory stimulation; and applying said periodic-exponential signal to the patient.

* * * * *